United States Patent
Madden et al.

(10) Patent No.: US 12,350,181 B2
(45) Date of Patent: Jul. 8, 2025

(54) LOWER LIMB ORTHOSIS

(71) Applicant: LB2 Technologies, LLC, Destin, FL (US)

(72) Inventors: William Byrne Madden, Fort Walton Beach, FL (US); Leo Chuen Chen, Destin, FL (US)

(73) Assignee: LB2 TECHNOLOGIES, LLC

( * ) Notice: Subject to any disclaimer, the term of this patent is extended or adjusted under 35 U.S.C. 154(b) by 23 days.

(21) Appl. No.: 16/840,158

(22) Filed: Apr. 3, 2020

(65) Prior Publication Data

US 2020/0315833 A1 Oct. 8, 2020

Related U.S. Application Data

(60) Provisional application No. 62/919,988, filed on Apr. 8, 2019.

(51) Int. Cl.
*A61F 5/01* (2006.01)

(52) U.S. Cl.
CPC .... *A61F 5/0127* (2013.01); *A61F 2005/0165* (2013.01)

(58) Field of Classification Search
CPC .. A61F 5/0127; A61F 5/01; A61F 5/00; A61F 5/0113; A61F 2005/0165; A61F 5/0111; A61F 5/019; A61F 5/0104; A61F 5/0585; A61F 5/058; A61F 5/37; A61F 5/05841; A43B 7/20; A41D 13/05; A41D 13/0543; A41D 13/06; A61H 3/00; A61H 3/007; A61B 5/6811; A61B 2019/502; A61B 2034/102
USPC .............................. 128/882; 602/23, 27, 28
See application file for complete search history.

(56) References Cited

U.S. PATENT DOCUMENTS

| | | | |
|---|---|---|---|
| 3,504,668 A * | 4/1970 | Boudon | A61F 5/0113 602/28 |
| 3,976,059 A | 8/1976 | Lonardo | |
| 4,393,866 A * | 7/1983 | Finnieston | A61F 5/0585 602/23 |
| 4,771,768 A | 9/1988 | Crispin | |
| 5,219,324 A | 6/1993 | Hall | |
| 5,269,748 A | 12/1993 | Lonardo | |
| 5,425,701 A | 6/1995 | Oster et al. | |
| 5,609,568 A * | 3/1997 | Andrews | A61F 5/0111 602/23 |

(Continued)

FOREIGN PATENT DOCUMENTS

| | | |
|---|---|---|
| CN | 1774222 A | 5/2006 |
| CN | 106535832 A | 3/2017 |

OTHER PUBLICATIONS

PCT/IB2020/000310, A Lower Limb Orthosis, Apr. 3, 2020.

*Primary Examiner* — Alireza Nia
*Assistant Examiner* — Daniel A Miller
(74) *Attorney, Agent, or Firm* — PERRY + CURRIER INC.

(57) ABSTRACT

An orthosis for a lower limb is provided. In one aspect, the orthosis is comprised of a shell that is portioned and dimensioned so as to be in close proximity to an anatomical limb. The shell has a leg portion, a foot portion, and a heel portion, the leg portion being fitted over the anterior surface of the leg, the foot portion being fitted over the dorsal surface of the foot, and the heel portion being fitted over the surface of the heel and adapted to lift the heel when a force is applied to the leg portion. The orthosis impedes dorsiflexion and permits plantarflexion.

10 Claims, 2 Drawing Sheets

(56) References Cited

U.S. PATENT DOCUMENTS

| | | | |
|---|---|---|---|
| 5,718,673 A | 2/1998 | Shipstead | |
| 5,776,090 A * | 7/1998 | Bergmann | A61F 5/0111 128/882 |
| 5,817,041 A | 10/1998 | Bader | |
| 6,692,454 B1 | 2/2004 | Townsend et al. | |
| 6,827,696 B1 | 12/2004 | Maguire | |
| 7,128,725 B2 | 10/2006 | Rabe | |
| D543,281 S | 5/2007 | Rabe | |
| 7,364,561 B1 * | 4/2008 | Morton | A61F 5/0127 128/882 |
| 8,425,440 B2 | 4/2013 | DeToro et al. | |
| 8,500,668 B2 | 8/2013 | Siegler et al. | |
| 8,708,942 B2 | 4/2014 | Kuhn | |
| 9,248,042 B2 | 2/2016 | Lopez et al. | |
| 2003/0153862 A1 | 8/2003 | Watts | |
| 2004/0102727 A1 * | 5/2004 | Smits | A61F 5/0111 602/28 |
| 2004/0236259 A1 * | 11/2004 | Pressman | A61F 5/0111 602/27 |
| 2007/0038169 A1 * | 2/2007 | Alon | A61F 5/0111 602/27 |
| 2007/0244420 A1 * | 10/2007 | Boden | A61F 5/0127 602/27 |
| 2008/0294083 A1 * | 11/2008 | Chang | A61F 5/0111 602/23 |
| 2011/0160632 A1 * | 6/2011 | Beckers | A61F 5/0127 602/27 |
| 2012/0065564 A1 * | 3/2012 | Hoffmeier | A61F 5/58 602/28 |
| 2012/0330206 A1 * | 12/2012 | George | A61F 5/0111 602/27 |
| 2013/0072841 A1 * | 3/2013 | Bader | A61F 5/0111 602/27 |
| 2014/0135675 A1 * | 5/2014 | Nayfa | A61F 5/01 602/27 |
| 2014/0288475 A1 | 9/2014 | Watts | |
| 2015/0011924 A1 * | 1/2015 | Messer | A61F 5/0102 264/223 |
| 2015/0305911 A1 * | 10/2015 | Schroeder | A61F 5/0113 602/28 |
| 2015/0320581 A1 | 11/2015 | Causse | |
| 2016/0220407 A1 * | 8/2016 | Jordan | A61F 5/0113 |
| 2016/0220408 A1 * | 8/2016 | Jordan | A61F 5/0111 |
| 2017/0000681 A1 * | 1/2017 | Adams | A61F 5/37 |
| 2017/0297278 A1 * | 10/2017 | LeCursi | B29C 70/28 |
| 2018/0200096 A1 * | 7/2018 | Jonsson | A61F 5/0111 |

\* cited by examiner

LOWER LIMB ORTHOSIS

FIELD

This application relates generally to orthoses for lower limbs.

BACKGROUND

In a normal gait cycle, the leg is first extended, placing the heel in contact with the ground and with the ankle in dorsiflexion. Then weight is transferred onto the foot which causes the foot to lie flat on the ground. Next, the weight is transferred from the heel region to the ball of the foot. Finally, the foot rotates from the ankle in a motion known as plantarflexion. Plantarflexion causes the heel to lift off the ground at the end of a stride. When the foot lifts off the ground, the normal gait cycle starts over again as the foot approaches heel strike.

A number of pathological conditions may interfere with a subject's ability to perform dorsiflexion or plantarflexion completely or correctly. For example, a partial or complete block of nerve function to the lower leg may hinder plantarflexion and/or dorsiflexion. Conditions such as diabetic nerve pain, drop foot, plantar fasciitis, traumatic nerve injury and demyelination, or iatrogenic nerve injury may cause abnormal foot and ankle movement during the gait cycle. Subjects experiencing these conditions may be unable to walk, run, or ride a bicycle normally. Walking with an altered gait or limp can contribute to pain, dysfunction, and deterioration of the knees, hips, and spine.

One solution is to provide electrical stimulation to foot and/or ankle muscles at appropriate times during ambulation. A number of orthoses incorporate electrodes that emit an electrical current causing muscles to contract even in the absence of a nerve signal. The electrical stimuli may be coordinated in response to signals from pressure sensors in the sole of the orthosis. However, these orthotic devices are expensive to manufacture and are limited by the battery life of the device. Additionally, the subject must carry a cumbersome controller that typically houses a bulky battery and a microprocessor. Another common solution is an ankle foot orthosis that consists of a posterior leg portion that extends into a plantar plate that blocks plantarflexion.

SUMMARY OF THE INVENTION

It is an aspect of the present invention to provide an orthosis that permits plantarflexion of the foot. The orthosis has a shell portioned and dimensioned to be in close proximity to the foot and leg of a subject. The shell has:
 (a) a leg portion that is fitted over the anterior surface of the leg;
 (b) a foot portion that is fitted over the dorsal surface of the foot and adapted to impede dorsiflexion of the foot: and
 (c) a heel portion that can lift the heel when a force is applied to the leg portion, The shell of the orthosis may be a single rigid form.

The foot portion of the orthosis may be flexible such that some degree of dorsiflexion is permitted.

The shell of the orthosis may be molded to the foot and leg of the subject.

The orthosis may be formed to support the foot in a specific angle of dorsiflexion.

The orthosis may be formed to support the foot in a range of angles of dorsiflexion.

The orthosis may have a component for securing the leg portion to the subject's leg, and particularly the lower leg, and subsequently releasing the leg portion from the subject's leg.

The orthosis may have a calf member fitted over the calf which may be secured to and subsequently released from the leg portion.

Some or all portions of the orthosis may be suitable for wearing inside footwear or under legwear such as shoes, boots, pants and/or trousers.

It is another aspect of the present invention to provide an orthosis that permits plantarflexion and has a shell portioned and dimensioned to be in close proximity to the foot and leg of a subject. The shell has:
 (a) a leg portion that is fitted over the anterior surface of the lower leg and can be secured to the leg and subsequently released.
 (b) a foot portion fitted over the dorsal surface of the foot that impedes dorsiflexion of the foot.
 (c) a heel portion that can lift the heel when an anterior force is applied to the leg portion.

The shell may be comprised of a single rigid form

The orthosis may be molded at 90 degrees of dorsiflexion of the foot.

The foot portion of the orthosis may be flexible to permit dorsiflexion between 75 and 105 degrees.

The orthosis may include a calf member fitted over the posterior of the leg which may be secured to and subsequently released from the leg.

The foot portion of the orthosis may include at least one toe portion fitted over the dorsal surface of one or more toes.

Some or all of the orthosis may be suitable for wearing inside footwear or legwear such as shoes, boots, and/or trousers.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

An orthosis for a lower limb is provided. In one aspect, the orthosis is comprised of a shell that is portioned and dimensioned so as to be in close proximity to an anatomical limb. The shell has a leg portion, a foot portion, and a heel portion, the leg portion being fitted over the anterior surface of the leg, the foot portion being fitted over the dorsal surface of the foot, and the heel portion being fitted over the surface of the heel and adapted to lift the heel when AN ANTERIOR force is applied to the leg portion. The orthosis impedes dorsiflexion and permits plantarflexion. In this disclosure, the term "impede" means that the orthosis may permit some degree of dorsiflexion, but dorsiflexion will be controlled or limited by the orthosis.

Figure 1:
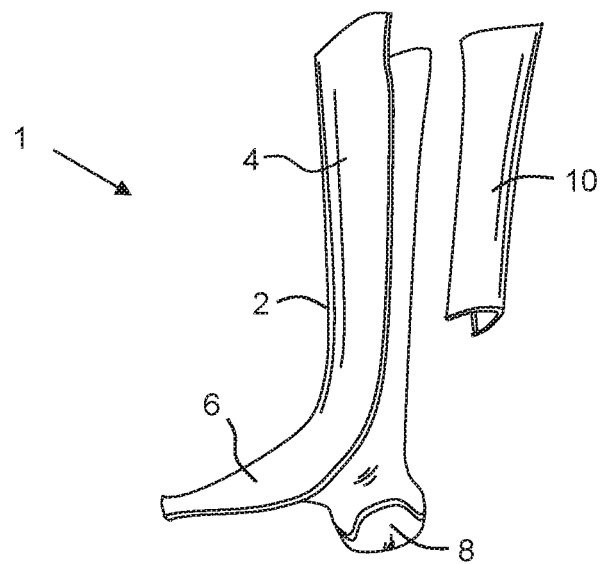
FIG. 1 shows a medial view of an orthosis 1 in accordance with various aspects and embodiments of the invention.

Referring to FIG. 1, an orthosis 1 is generally shown. The orthosis comprises a shell 2 having a leg portion 4, a foot portion 6, and a heel portion 8.

The foot portion 6 is fitted over the dorsal surface of the foot and is adapted to impede dorsiflexion of the foot. The dorsal surface of the foot covered by the foot portion 6 may extend from the ankle to a distal point, such as to a point behind the toes, or in some embodiments, and particularly embodiments in which some or all of the foot portion is flexible, to a point covering some or all of the upper portions of some or all of the toes. It is contemplated that the foot portion 6 may be a sufficient length to impede dorsiflexion. For example, the foot portion 6 may be fitted over an area from the ankle to the metatarsals. In another implementation, the foot portion 6 may be fitted over an area from the ankle to the phalanges. It is further contemplated that the length of the foot portion may be adapted to fit the proportions of the subject.

The heel portion 8 is fitted beneath the heel and is adapted to lift the heel when an anterior force is applied to the leg portion. Lifting the heel may be accomplished by leveraging this force applied to the leg portion 4. For example, when weight is transferred from the proximal region of the foot to the distal region of the foot during ambulation, the leg may push against the leg portion 4 of the shell 2 causing the heel portion 8 to lift the heel. This plantarflexion action may assist a subject in lifting the heel during ambulation, walking, running, bicycling, or other activities requiring motion of the leg. Production of a leveraging force via plantarflexion may be accomplished by providing heel portion 8 shaped to cup the heel from below, as an integral part of shell 2, or as a relatively rigidly attached portion of the shell 2.

Figure 2:
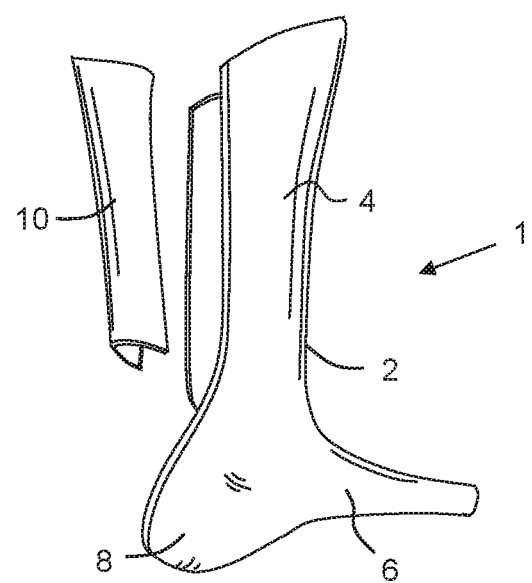
FIG. 2 shows a lateral view of the orthosis 1.

The heel portion 8 may be connected to the shell 2 on either the medial or lateral side or both sides. FIGS. 1 and 2 depict an orthosis 1 having a heel portion 8 connected to the shell 2 on the lateral side. The heel portion 8 may cover a sufficient portion of the plantar surface of the heel to facilitate lifting of the heel when a force is applied to the leg portion 4. The heel portion 8 may additionally cover a portion of the posterior surface of the heel to impede slippage of the orthosis during use. The heel portion 8 may be portioned and dimensioned to cup the heel, as shown in FIG. 1.

The leg portion 4 is fitted across the anterior surface of the leg, including for example some or all of the shin. The surface of the leg covered by the leg portion 4 may extend from an anterior portion of the ankle, including some of the upper portion of the foot, to a point below the knee. In one implementation, the leg portion 4 may extend from an anterior portion of the ankle to a point just below the tibial tubercle. It is contemplated that the leg portion 4 may be a sufficient length to provide a pivot for lifting the heel. The leg portion, heel portion, and foot portion may comprise a continuous, rigid form. The leg portion may additionally be fitted to a lateral and/or medial surface of the leg. In particular, the leg portion 4 may be contoured around the lateral and/or medial surface of the leg to prevent slippage of the shell 2 relative to the leg. It is further contemplated that the length of the leg portion may be adapted to fit the proportions of the subject.

The orthosis 1 has a form adapted to permit plantarflexion of the foot. In the implementation shown in FIG. 1, the orthosis is fitted to the heel but otherwise is not fitted to the plantar surface of the foot. Only the heel portion of the orthosis is configured to fit over the plantar portion of the foot. This implementation may permit the foot to rotate in plantarflexion. Additionally, this implementation may permit the toes to also plantarflex. This implementation may facilitate the toes to press down against the ground during ambulation creating more leverage for the orthosis and assisting the gait cycle.

The orthosis may further comprise a calf member 10 fitted over a posterior surface of the leg. The calf member may additionally cover a lateral and/or medial surface of the leg. The calf member 10 may be releasably attached to the leg and/or the leg portion 4 of the shell 2. The calf member 10 may impede slippage of the orthosis 1 relative to the leg when in use. In some implementations, the calf member 10 may be molded to the leg of a subject to provide a close fit. The calf member 10 may comprise a flexible or rigid material. In some implementations, the calf member 10 comprises a polymer. In further implementations, the calf member 10 may comprise any or all of low density polyethylene, polypropylene, graphite, carbon fiber and a copolymer mix.

The shell 2 may be a single form and is optionally rigid, semi-rigid, or semi-flexible. The leg portion, heel portion, and foot portion may be a monolithic, rigid form. In some implementations, the rigidity of the shell 2 will not be consistent throughout all portions of the shell 2. It is contemplated that the degree of rigidity in some or all portions of the shell 2 facilitates the foot portion to selectively impede dorsiflexion of the foot without causing discomfort to the wearer. In particular, it is contemplated that a particular rigidity of the foot portion 6 may be selected to permit dorsiflexion within a range of desired angles. It is further contemplated that rigidity of some or all portions of the shell 2 facilitates desired positioning of the heel portion 8 in conjunction with the leg portion 4 to lift the heel during ambulation. In some implementations, the shell is contoured or molded to the subject's leg and foot. The shell 2 may comprise a polymer. In further implementations, the shell 2 comprises any or all of low density polyethylene, polypropylene, graphite, carbon fiber or a copolymer mix. In order to prevent discomfort for the wearer, some or all of the interior surface(s) of the orthosis may be covered, or otherwise cooperate, with padded material.

The shell 2 may be dimensioned so as to be unobtrusive when worn under clothing or footwear.

The shell 2 may be portioned and dimensioned to a specific range of dorsiflexion of the foot. In one implementation, the shell 2 may be portioned and dimensioned to an angle of approximately 105°. In an additional implementation, the shell may be portioned and dimensioned to an angle of approximately 95°. In another implementation, the shell 2 may be portioned and dimensioned to an angle of approximately 85°. In a yet further implementation, the shell 2 may be portioned and dimensioned to an angle of approximately 75°.

In some implementations, the shell 2 may be portioned and dimensioned to permit some degree of dorsiflexion. The shell may be portioned and dimensioned to permit dorsiflexion of the foot between 75 and 105 degrees. The shell 2 may be dimensioned such that certain portions of the shell may have different thicknesses. In other implementations, certain portions of the shell 2 may have different rigidities or flexibility. For example, the foot portion 6 may have a thickness such that a specific degree of dorsiflexion is permitted. It is contemplated that the shell 2 may be portioned and dimensioned either in a specific angle of dorsiflexion or in an assortment of dorsiflexion angles to provide the optimal combination of comfort and function for the wearer.

The shell 2 is not necessarily a single form. In some implementations, the foot portion 6 may be connected to the leg portion 18 of the orthosis. For example, the foot portion may be connected to the leg portion 18 with an articulated joint, hinge, or other suitable attachment mechanism (not shown). It is contemplated that the attachment mechanism may accommodate dorsiflexion of the foot through a limited range of angles.

Figure 3:
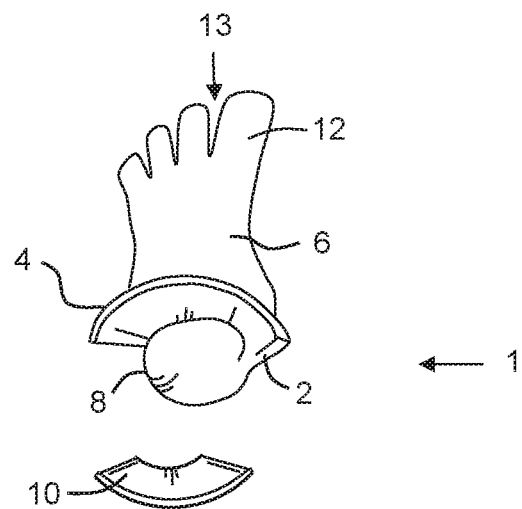
FIG. 3 shows a top view of the orthosis 1.

FIG. 3 shows a top view of the orthosis 1. In this implementation, the foot portion 6 of the shell 2 includes toe members 12. The shell 2 may have one or more toe members 12. The toe members 12 may be extensions of the shell 2 that are portioned and dimensioned to be in close proximity to one or more toes. The toe members may impede, limit, or otherwise selectively control dorsiflexion of the phalanges of the respective toes. Some or all of toe members 12 may be separated by gaps 13. The gaps 13 may allow the orthosis 1 to be worn with a variety of footwear including but not limited to sandals, flip flops, and athletic footwear.

Figure 4:
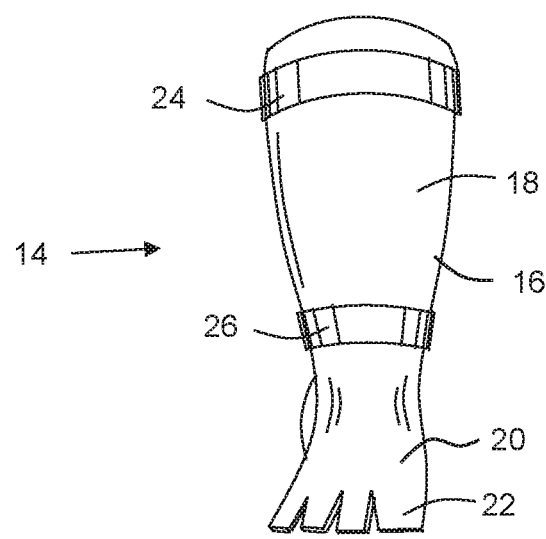
FIG. 4 shows a front view of another orthosis 14.

FIG. 4 shows a front view of another embodiment of an orthosis 14. The orthosis 14 may have a shell 16 that includes a leg portion 18, a foot portion 20, and a heel portion (not shown). The foot portion 20 may include toe members 22. The leg portion 18 may be releasably secured to the leg. Additionally, the calf member (not shown) may be releasably secured to the leg or the leg portion 18 with straps. In FIG. 4, the leg portion 18 is releasably secured to the leg with one or more straps 24, 26, however the means of releasably securing the leg portion to the leg is not limited to straps. The means of releasably securing the leg portion to the leg may include buckles, hook and loop fasteners, laces, belts, buttons, Velcro®, elasticized material, or other fasteners. Similarly, the means of releasably securing the calf member to the leg or the leg portion 18 may include buckles, hook and loop fasteners, laces, belts, buttons, Velcro®, elasticized material or other fasteners.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

I claim:

1. An orthosis comprising a shell configured to be in close proximity to an anatomical foot and leg, said shell comprising:
   a leg portion configured to fit over an anterior surface of the leg;
   a foot portion configured to fit over a dorsal surface of the foot and configured to impede dorsiflexion of the foot, the foot portion consisting of a heel portion configured to fit over a heel of the foot and adapted to lift the heel when an anterior force is applied to the leg portion, the heel portion connected to the foot portion on a single side of the orthosis and configured to leave a gap on an opposite side of the orthosis to receive the foot;
   wherein the shell is formed in a specific angle of dorsiflexion of the foot;
   wherein the leg portion, heel portion, and foot portion comprise a monolithic, rigid form; and
   a plurality of toe portions with gaps therebetween, the plurality of toe portions configured to be in close proximity to a plurality of toes of the foot;
   wherein only the heel portion of the shell of the orthosis is configured to fit over a plantar portion of the foot such that the orthosis permits plantarflexion of the foot.

2. The orthosis of claim 1 wherein the shell is configured to be molded to the foot and leg.

3. The orthosis of claim 1 wherein the specific angle of dorsiflexion is 90 degrees.

4. The orthosis of claim 1 further comprising straps, buckles, hook and loop fasteners, laces, belts, buttons, or elasticized material for releasably securing the leg portion to the leg.

5. The orthosis of claim 1 further comprising a calf member configured to fit over a posterior of the leg, wherein the calf member is configured for releasably securing to the leg.

6. The orthosis of claim 1, the orthosis being configured to be worn inside footwear.

7. An orthosis comprising a shell configured to be in close proximity to an anatomical foot and leg, said shell comprising:
   a leg portion configured to fit over an anterior surface of the leg and configured for releasably securing to the leg;
   a foot portion configured to fit over a dorsal surface of the foot and configured to impede dorsiflexion of the foot, the foot portion consisting of a heel portion configured to fit over a portion of a plantar surface of the foot and to lift a heel of the foot when a force is applied to the leg portion, the heel portion connected to the foot portion on a single side of the orthosis and configured to leave a gap on an opposite side of the orthosis to receive the foot;
   wherein the shell is formed in a specific angle of dorsiflexion of the foot;
   wherein the leg portion, heel portion, and foot portion comprise a monolithic, rigid form; and
   a plurality of toe portions with gaps therebetween, the plurality of toe portions configured to be in close proximity to a plurality of toes of the foot;
   wherein only the heel portion of the shell of the orthosis is configured to fit over a plantar portion of the foot such that the orthosis permits plantarflexion of the foot.

8. The orthosis of claim 7 wherein the specific angle of dorsiflexion is 90 degrees.

9. The orthosis of claim 7 further comprising a calf member configured to fit over a posterior of the leg, wherein the calf member is configured for releasably securing to the leg.

10. The orthosis of claim 7, the orthosis being configured to be worn inside footwear and clothing.

* * * * *